US011899001B2

(12) United States Patent
Makaram et al.

(10) Patent No.: US 11,899,001 B2
(45) Date of Patent: Feb. 13, 2024

(54) METHOD FOR PROVIDING CALIBRATION DATA FOR A GAS SENSOR DEVICE, METHOD OF CALIBRATING A GAS SENSOR DEVICE, AND PROCESSING DEVICE FOR A GAS SENSOR DEVICE

(71) Applicant: Infineon Technologies AG, Neubiberg (DE)

(72) Inventors: Prashanth Makaram, Berlin (DE); Ulrich Krumbein, Rosenheim (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 432 days.

(21) Appl. No.: 16/692,489

(22) Filed: Nov. 22, 2019

(65) Prior Publication Data

US 2020/0166492 A1 May 28, 2020

(30) Foreign Application Priority Data

Nov. 23, 2018 (EP) .................................... 18208088

(51) Int. Cl.
*G01N 33/00* (2006.01)
*G01N 27/414* (2006.01)
*G06F 1/3203* (2019.01)

(52) U.S. Cl.
CPC ..... *G01N 33/0006* (2013.01); *G01N 27/4146* (2013.01); *G01N 33/0008* (2013.01);
(Continued)

(58) Field of Classification Search
CPC ........... G01N 27/4146; G01N 33/0008; G01N 33/0062; G01N 33/0073; G01N 2033/0068

See application file for complete search history.

(56) References Cited

U.S. PATENT DOCUMENTS 4,849,798 A * 7/1989 Wantanabe .......... G01N 27/414
257/253
5,719,033 A * 2/1998 Ackley ................ G01N 27/414
204/422
(Continued)

FOREIGN PATENT DOCUMENTS

CN 106289887 A * 1/2017 ................ G01N 1/22
CN 108732226 A * 11/2018 ........... G01N 27/416
(Continued)

OTHER PUBLICATIONS

CN-108732226-A—English Translation (Year: 2018).*
CN-106289887-A—English Translation (Year: 2017).*
Zhang, Run, et al. "Highly sensitive acetone gas sensor based on g-C3N4 decorated MgFe2O4 porous microspheres composites." Sensors 18.7 (2018): 2211. (Year: 2018).*
(Continued)

*Primary Examiner* — Kristina M Deherrera
*Assistant Examiner* — Fatemeh Esfandiari Nia
(74) *Attorney, Agent, or Firm* — Slater Matsil, LLP

(57) ABSTRACT

A method includes exposing gas sensitive material of a gas sensor device to different adjusted target gas concentrations, determining measurement values of the resistance of the gas sensitive material between first and second contact regions in response to the adjusted target gas concentration, determining a first gas sensor behavior model based on the measurement values of the resistance of the gas sensitive material as a function of the adjusted target gas concentration, translating the first gas sensor behavior model into a corresponding second gas sensor behavior model for the resistance of the gas sensitive material as a function of a control voltage, and sweeping the control voltage based on the second gas sensor behavior model over a control voltage range for providing control voltage dependent resistance data, wherein the control voltage dependent resistance data over the control voltage range form the calibration data for the gas sensor device.

15 Claims, 8 Drawing Sheets

(52) U.S. Cl.
CPC ..... *G01N 33/0062* (2013.01); *G01N 33/0073* (2013.01); *G06F 1/3203* (2013.01); *G01N 2033/0068* (2013.01)

(56) References Cited

U.S. PATENT DOCUMENTS

| | | |
|---|---|---|
| 5,789,659 A | 8/1998 | Williams |
| 2003/0037590 A1 | 2/2003 | Stark |
| 2006/0174683 A1 | 8/2006 | Bonne et al. |
| 2009/0126454 A1 | 5/2009 | Pratt et al. |
| 2013/0180854 A1 | 7/2013 | Sasaki |
| 2018/0120253 A1* | 5/2018 | Sasago ............... H01L 29/4966 |
| 2019/0145929 A1* | 5/2019 | Carbonelli ......... G01N 33/0042 204/424 |
| 2020/0110060 A1* | 4/2020 | Park ..................... G01N 29/022 |
| 2020/0158710 A1* | 5/2020 | Mazzillo ............. G01N 27/129 |
| 2020/0256826 A1* | 8/2020 | Chen ................... G01N 27/4146 |
| 2021/0181134 A1* | 6/2021 | Martin ................ G01N 33/0006 |
| 2021/0262976 A1* | 8/2021 | Tobjork ............... G01N 27/126 |

FOREIGN PATENT DOCUMENTS

| | | |
|---|---|---|
| EP | 0751392 A2 | 1/1997 |
| RU | 2341790 C1 | 12/2008 |
| WO | WO-2018204780 A1 * | 11/2018 |

OTHER PUBLICATIONS

Domansky, Karel et al., "Development and Calibration of Field-Effect Transistor-Based Sensor Array for Measurement of Hydrogen and Ammonia Gas Mixtures in Humid Air", Analytical Chemistry, vol. 70, No. 3, Feb. 1, 1998, XP002926318, pp. 473-481.

Zhang, Zhangyuan, et al., "Hydrogen gas sensor based on metal oxide nanoparticles decorated graphene transistor", Nanoscale, Royal Society of Chemistry, 7, Mar. 2015, pp. 10078-10084.

K. Domansky et al., "Development and Calibration of Field-Effect Transistor-Based Sensor Array for Measurement of Hydrogen and Ammonia Gas Mixtures in Humid Air" Analytical Chemistry, vol. 70, Issue 3, Feb. 1, 1998, pp. 473-481.

J. Chen et al., "Carbon nanotube thin-film-transistors for gas identification" Elsevier, Sensors & Actuators B: Chemical 281, 2019, 1080-1087.

* cited by examiner cross section

Top view of 4 sensor array

METHOD FOR PROVIDING CALIBRATION DATA FOR A GAS SENSOR DEVICE, METHOD OF CALIBRATING A GAS SENSOR DEVICE, AND PROCESSING DEVICE FOR A GAS SENSOR DEVICE

This application claims the benefit of European Application No. 18208088.7, filed on Nov. 23, 2018, which application is hereby incorporated herein by reference.

TECHNICAL FIELD

Embodiments relate to a method and apparatus for a calibration of gas sensors. To be more specific, embodiments relate to a method for providing calibration data for a gas sensor device, to a method of calibrating or testing a gas sensor device, to a gas sensor arrangement having a processing device for a gas sensor device for providing calibration data and/or for calibrating or testing the gas sensor device. Embodiments also relate to a baseline calibration of a gas sensor device.

BACKGROUND

The detection of environmental parameters, e.g. gas concentrations, in the ambient atmosphere is becoming increasingly important in the implementation of appropriate sensors within mobile devices, but also in the application in home automation, such as smart home and, for example, in the automotive sector. However, with the evermore extensive use of gas sensors, there is also a particular need to be able to determine the functionality of such sensors, i.e., to provide appropriate calibration data for such gas sensor devices and for calibrating/testing such gas sensor devices. Such a calibration process should be inexpensively and cost-effectively implemented. To be more specific, a necessary calibration and final test for gas sensor devices is an expensive process. Especially, if the final use case or application of the gas sensor device, i.e., the set of relevant gases to be detected and qualified, is constantly changing.

Usually, a gas sensor calibration and testing is conducted by exposing the sensor device to a known gas or gas mixture in a dedicated chamber and by checking the variation in the base line resistance are zero of the gas sensor device. This approach is applicable for single gas or single use cases. However, this approach has severe limitations as soon as the sensor device has to be calibrated for multiple use cases/gases, e.g. multiple gases or gas mixtures. For multiple use cases, it is usually necessary to build a very generic test chamber posing the risk of a cross contamination, or to provide multiple dedicated test chambers for each use case resulting in strongly increased expenses and cost. On the technical field of base line calibrations, a base line calibration of a gas sensor device is usually carried out by assuming that the gas sensor device is in a "clean" environment, wherein based on this assumption, drifts of the gas sensor device in the base line resistance values $R_0$ is (tried to be) corrected. This is a very speculative process as the gas sensor device cannot distinguish between a sufficiently "clean" environment and an environment of a low concentration of the target gas.

Generally, there is a need in the art for an approach to implement an improved gas sensor calibration and testing and to efficiently provide calibration data for a gas sensor device.

Such a need can be solved for the subject-matter of the independent claims. Further specific implementations of the present concept (method and apparatus) for providing calibration data for a gas sensor device and for calibrating/testing a gas sensor device are defined in the dependent claims.

SUMMARY

According to an embodiment, a method is configured to provide calibration data for a gas sensor device, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, the method comprising: exposing the gas sensitive material of the gas sensor device to different adjusted target gas concentrations of a target gas, determining measurement values of the resistance of the gas sensitive material between the first and second contact region in response to the adjusted target gas concentration, determining a first gas sensor behavior model based on the measurement values of the resistance of the gas sensitive material as a function of the adjusted target gas concentration, translating the first gas sensor behavior model into a corresponding second gas sensor behavior model for the resistance of the gas sensitive material of the gas sensor device as a function of the control voltage applicable to the control electrode, and sweeping the control voltage based on the second gas sensor behavior model over a control voltage range for providing control voltage dependent resistance data, wherein the provided control voltage dependent resistance data or data derived therefrom over the control voltage range of the gas sensor device form the calibration data for the gas sensor device.

According to an embodiment, a method is configured to calibrate a gas sensor device, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, the method comprising: applying a control voltage to the control electrode of the gas sensor device, determining measurement values of the resistance of the gas sensor device in response to the control voltage applied to the control electrode of the gas sensor device, providing calibration data for the gas sensor device, wherein the calibration data for the gas sensor device comprise the control voltage dependent resistance data over the control voltage range of the gas sensor device, comparing the measurement values of the resistance of the gas sensor device with the calibration data, and adapting the output signal of the gas sensor device based on a measured difference between the measurement value of the resistance of the gas sensor device and the calibration data.

According to an embodiment, a method is configured to provide the calibration data for the gas sensor device in accordance to the method for providing calibration data for a gas sensor device.

According to an embodiment, a processing device for a gas sensor device is configured to provide calibration data, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, wherein the processing device is configured to: determine measurement values of the resistance of the gas sensitive material in response to the adjusted target gas concentration, during exposing the gas sensitive material of the gas sensor device to an adjusted target gas concentration, determine a first gas sensor behavior model based on the measurement values of the resistance of the gas sensitive material as a function of the adjusted target gas concentration, to translate the first gas sensor behavior model into a corresponding second gas sensor behavior model for the resistance of the gas sensitive material as a function of the control voltage applicable to the control electrode, and to sweep the control voltage based on the second gas sensor behavior model over a control voltage range for providing the control voltage dependent resistance data, wherein the provided control voltage dependent resistance data over the control voltage range of the gas sensor device or data derived therefrom form the calibration data for the gas sensor device.

According to an embodiment, a processing device for a gas sensor device is configured to calibrate a gas sensor device, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, wherein the processing device is configured to: apply a control voltage to the control electrode of the gas sensor device, determine measurement values of the resistance of the gas sensor device in response to the control voltage applied to the control electrode of the gas sensor device, provide calibration data for the gas sensor device, wherein the calibration data for the gas sensor device comprise the control voltage dependent resistance data over the control voltage range of the gas sensor device, compare the measurement values of the resistance of the gas sensor device with associated calibration data, and adapt the output signal of the gas sensor device based on a measured difference between the measurement value of the resistance of the gas sensor device and the associated calibration data.

According to an embodiment, the processing device for calibrating a gas sensor device is further configured to provide the calibration data for the gas sensor device.

BRIEF DESCRIPTION OF THE DRAWINGS

Embodiments of the present methods for providing calibration for a gas sensor device and for calibrating/testing a gas sensor device and embodiments of the gas sensor arrangement for providing calibration data and/or for calibrating the gas sensor device are described herein making reference to the appended drawings and figures.

Before discussing the present embodiments in further detail using the drawings, it is pointed out that in the figures and the specification identical elements and elements having the same functionality and/or the same technical or physical effect are usually provided with the same reference numbers or are identified with the same name, so that the description of these elements and of the functionality thereof as illustrated in the different embodiments are mutually exchangeable or may be applied to one another in the different embodiments.

DETAILED DESCRIPTION OF ILLUSTRATIVE EMBODIMENTS

In the following description, embodiments are discussed in detail, however, it should be appreciated that the embodiments provide many applicable concepts that can be embodied in a wide variety of semiconductor devices. The specific embodiments discussed are merely illustrative of specific ways to make and use the present concept, and do not limit the scope of the embodiments. In the following description of embodiments, the same or similar elements having the same function have associated therewith the same reference signs or the same name, and a description of these elements will not be repeated for every embodiment. Moreover, features of the different embodiments described hereinafter may be combined with each other, unless specifically noted otherwise.

It is understood that when an element is referred to as being "connected" or "coupled" to another element, it may be directly connected or coupled to the other element, or intermediate elements may be present. Conversely, when an element is referred to as being "directly" connected to another element, "connected" or "coupled," there are no intermediate elements. Other terms used to describe the relationship between elements should be construed in a similar fashion (e.g., "between" versus "directly between", "adjacent" versus "directly adjacent", and "on" versus "directly on", etc.).

Figure 1A:
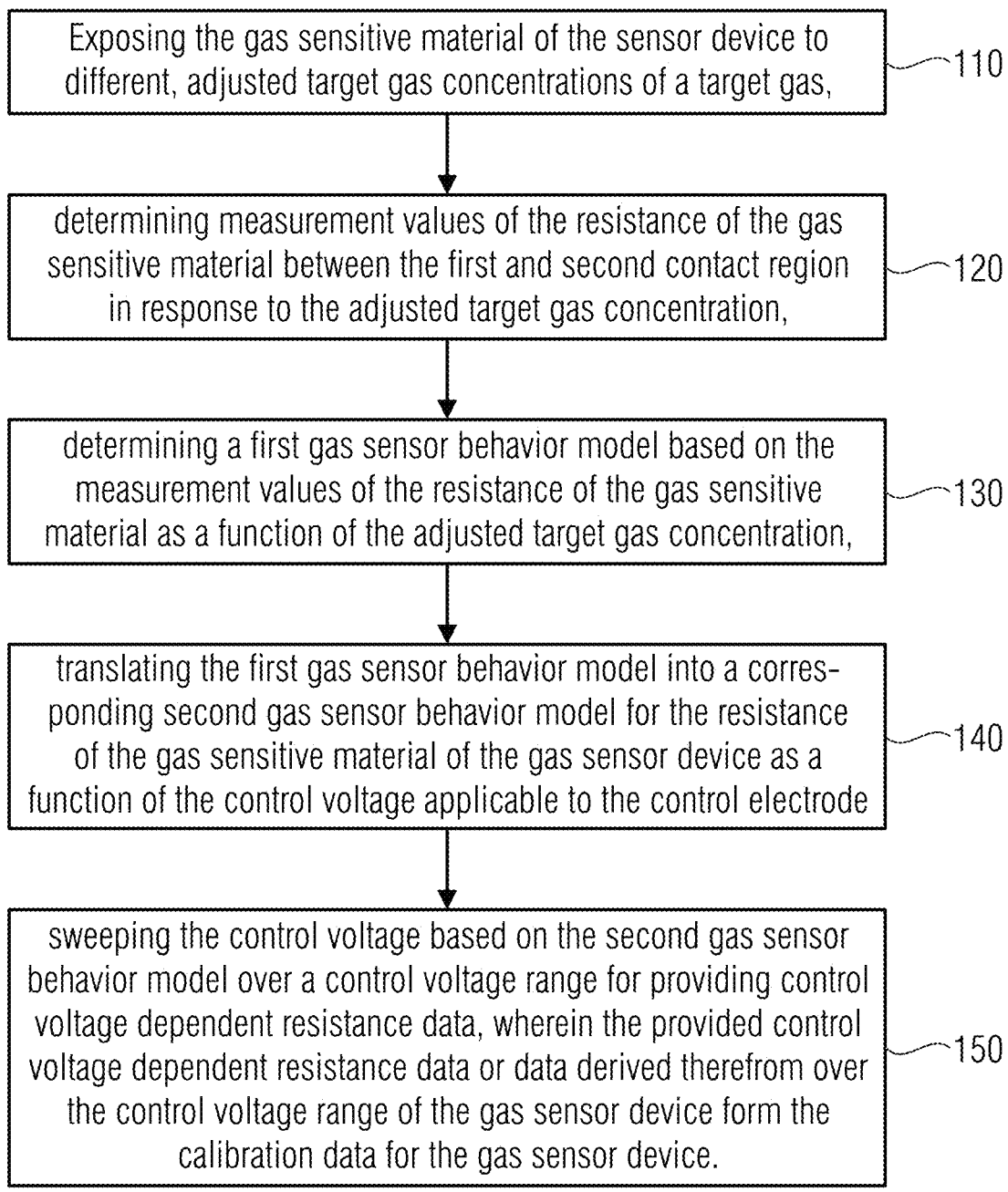
FIG. 1a shows an exemplary process flow (flowchart) of the method for providing calibration data for a gas sensor device according to an embodiment.
Figure 1B:
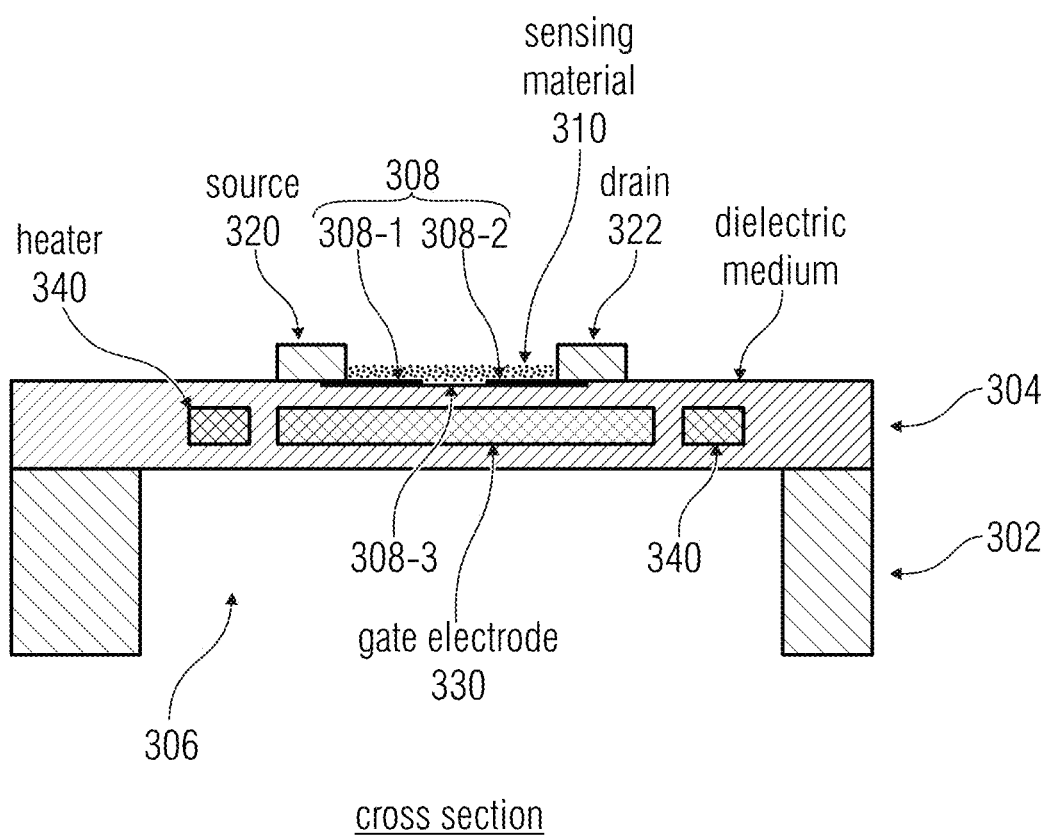
FIG. 1b shows a schematic cross sectional view of a gas sensor device according to an embodiment.

FIG. 1a shows an exemplary process flow or flowchart of a method 100 for providing calibration data for a gas sensor device 300 according to an embodiment. FIG. 1b shows a schematic cross sectional view of a gas sensor device 300 according to an embodiment. As shown in FIG. 1b, the gas sensor device 300 comprises a gas sensitive material (=gas sensing element) 310, which is electrically arranged between a first contact region (source) 320 and a second contact region (drain) 322, and a control electrode (gate) 330, which is arranged neighboring to the gas sensitive material 310. The resistance $R_{DS}$ of the gas sensitive material 310 between the first contact region 320 and the second contact region 322 has a dependency on a concentration or quantity of an environmental target gas and has also a dependency on a control voltage (gate voltage) $V_G$ applicable to the control electrode 330.

With respect to the specific arrangement of the different elements of the gas sensor device 300, it is further referred to FIGS. 6a-6b and the associated description of the technical functionality as described below.

As shown in FIG. 1b, the gas sensor device may further optionally comprise a heating element 340 neighboring to the gas sensitive material 310 for heating the environmental target gas and/or the gas sensitive material 310 to a further measuring temperature $T_{M1}$, which is higher than the "normal" ambient temperature $T_M$.

As shown in FIG. 1b, the gas sensor device 300 can be implemented as a MEMS die (chip) having a substrate 302, a membrane 304 having a dielectric material, e.g. a silicon nitride (SiN) membrane, a Bosch cavity 306 in the substrate 302, a top electrode 308 onto which the (functionalized) sensing material 310 is arranged or dispensed, and the heating element(s) 340, e.g. in form of a (highly doped) polysilicon heater. The gas sensitive material (=gas sensitive element) 310 may be arranged in form of a layer or of nanotubes etc. comprising the gas sensitive material.

The top electrode 308 may comprise two metal pads 308-1, 308-2, e.g. Ti/Au, which are separated by a gap 308-3 therebetween and which are connected to the first contact region (source) 320 and the second contact region (drain) 322, respectively. The sensitive material 310 is dispensed in such a way that it bridges the gap 308-3 between the two metal pads 308-1, 308-2 of the top electrodes 308, thus creating a conductive path.

In this configuration, the material of the control electrode (=the gate material) 330 may comprise, for example, a highly doped polysilicon material, and may be embedded into the membrane 304. The control electrode 330 may be formed on the same layer as the heater element 340. The sensor configuration as shown in FIG. 1b is called a "bottom gate" configuration. However, embodiments of the gas sensor device 300 do not have to be restricted to a bottom gate configuration, wherein the gas sensor device 300 also works with a "top gate configuration" (not shown in FIG. 1b), wherein the control electrode 330 may be formed on the opposing side (=top side) of the gas sensitive material 310. The gas sensor device 300 even works with a configuration (not shown in FIG. 1b), where the control electrode (gate) 330 is not attached directly to the silicon substrate 302 or the membrane 304 but at a plate (not shown in FIG. 1b) that is placed at a distance "x" from the gas sensitive material 310 of the gas sensor device 300. A processing device (not shown in FIG. 1b) may be connected to the gas sensor device 300 and may be configured to conduct the method 100 as shown in FIG. 1a.

The method 100 for providing the calibration data for the gas sensor device 300 comprises a step 100 of exposing the gas sensitive material 310 of the gas sensor device 300 to the different adjusted target gas concentrations of the target gas. In step 120, measurement values of the resistance $R_{DS}$ of the gas sensitive material 310 between the first and second contact regions 320, 322 are determined in response to the adjusted target gas concentration. To be more specific, the gas sensitive material 310 is exposed to the target gas having the adjusted target gas concentration in the environmental atmosphere.

During the step 120 of determining measurement values of the resistance $R_{DS}$ of the gas sensitive material 310, a predetermined control voltage $V_G$ may be applied to the control electrode 330, wherein, according to a further embodiment, the control electrode 330 may be in a floating condition, i.e. may form a floating gate control electrode 330, with a zero control voltage $V_G$=0.

A typical value of the control voltage Vg is between ±100 mV to ±10V (or more precisely between ±100 mV to ±1V). Depending on the dielectric material used for the membrane 304 and its thickness this value can go up to 30 V, for example.

In step 130, a first gas sensor behavior model is determined based on the measurement values of the resistance $R_{DS}$ of the gas sensitive material 310 of the gas sensor device 310 as a function of the adjusted target gas concentration. The first gas sensor behavior model, e.g., in form of a fitting function or a parametric model of the gas sensor behavior, is based on the dependency of the resistance $R_{DS}$ of the gas sensitive material 310 from the adjusted target gas concentration to which the gas sensitive material 310 is exposed.

In step 140, the first gas behavior model is translated into a corresponding second gas sensor behavior model for the resistance $R_{DS}$ of the gas sensitive material 310 of the gas sensor device 300 as a function of the control voltage $V_G$ applicable to the control electrode 330. According to an embodiment, the first gas sensor behavior model is translated into the corresponding sensor behavior model for the resistance $R_{DS}$ of the gas sensor device 310 based on the dependency of the resistance $R_{DS}$ of the gas sensitive material 310 from the control voltage $V_G$.

In step 150, the control voltage $V_G$ is swept or tuned based on the second gas sensor behavior model over a control voltage range $_\Delta V_G$ for providing control voltage dependent resistance data. The provided control voltage dependent resistance data over the control voltage range $_\Delta V_G$ of the gas sensor device 300 or data derived therefrom form the calibration data for the gas sensor device 300. In other words, the calibration data for the gas sensor device 300 are derived or determined on the basis of the provided control voltage dependent resistance data over the control voltage range $_\Delta V_G$ of the gas sensor device 300.

Thus, in step 150 the gate voltage (=control voltage) $V_G$ may be swept based on the sensor device behavior model to replicate sensor device behavior. By running more than one gate sweep for reproducing multiple concentrations of the target gas, the calibration data for the gas sensor device 300 can be extracted.

According to an embodiment, the control voltage dependent resistance data of the gas sensor device 300 depend on the frequency and/or the amplitude of the control voltage $V_G$.

The control voltage range $_\Delta V_G$ is the range of the gate voltage $V_G$ that is needed to replicate the behavior sensing material's resistance $R_{DS}$ to the different gases of interest. The range of this voltage $V_G$ may depend on:
- The dielectric material ($SiO_2$, $HF_2$, etc.) of the membrane 304,
- The thickness of the dielectric material,
- The channel length (width of the gap 308-3),
- The type of graphene composite. (For example with a p-type semiconductor, the Vg>0, and similarly for an n-type semiconductor Vg<0).

According to an embodiment, the different values of the control voltage $V_G$ over the control voltage range $_\Delta V_G$ correspond to different target gas concentrations at a measuring temperature $T_M$.

According to an embodiment, the step of determining measurement values of the resistance of the gas sensitive material may be repeated for different target gas concentrations and/or for different target gas compositions and/or for different measuring temperatures $T_M$, $T_{M1}$, etc.

As described above, the gas sensor device 300 may further comprises the heating element(s) 340 neighboring to the gas sensitive material 310. According to an embodiment, the method 100 may further comprise the step of activating the heating element 340 for heating the environmental target gas and/or the gas sensitive material 310 to a further measuring temperature $T_{M1}$, and additionally conducting the steps of exposing 110 the gas sensor device, determining 120 measurement values, determining 130 a first gas sensor behavior model, translating 140 the first gas sensor behavior model into a second gas sensor behavior model, and sweeping 150 the control voltage for the further measuring temperature $T_{M1}$, and determining the control voltage dependent resistance data over the control voltage range also for the further measuring temperature(s) $T_{M1}$, $T_{M2}$, . . . .

According to an embodiment, the heating element(s) 340 may optionally provide a number of functionalities achieved by heating the gas sensitive material 310, for example. The sensitivity of the gas sensitive material 310, e.g. a graphene material may be increased. Different environmental and target gas temperatures may be simulated during the calibration data provision process and/or calibration process. A correction of the baseline resistance $R_o$ may be conducted. Moreover, the gas sensitive material 310 (=the functionalized material) may be "reset", e.g. brought in a defined condition or initial condition. Moreover, a poisoning of the gas sensitive material 310 may be removed, for example.

According to an embodiment, the calibration data may be on a memory device (not shown in FIG. 1b) to which the gas sensor device 300 or the processing device of the gas sensor device 300 may have access.

According to an embodiment, the method 100 may further comprise the steps of determining a control voltage dependent measurement value of the resistance $R_{DS}$ of the gas sensitive material having (within a tolerance range) a minimum sensitivity or a complete insensitivity to the target gas concentration, and storing the determined control voltage dependent measurement value as a baseline calibration value $R_o$ in the memory device accessible to the gas sensor device 300.

According to an embodiment, the method 100 may further comprise the steps of determining the control voltage dependent measurement value of the resistance $R_{DS}$ of the gas sensitive material 310 having (within a tolerance range) a minimum sensitivity or complete insensitivity to the target gas concentration for different temperatures $T_{M1}$, $T_{M2}$ of the environmental target gas and/or of the gas sensitive material 310, and storing the determined control voltage dependent measurement value as the baseline calibration value Ro in the memory device accessible to the gas sensor device 300, wherein the baseline calibration value Ro is also independent of the temperature of the environmental target gas and/or the gas sensitive material 310 exposed to the target gas.

To summarize, the resistive gas sensitive material 310 shows, among others, a dependency of the conductivity and the resistance (resistivity), respectively, on the surrounding gas, i.e. with the gas molecules interacting with the sensor material 310 and, further, on the control voltage ("bias") applied to the control electrode 330.

Due to the dependency of the conductivity of the gas sensitive material, e.g. a graphene comprising layer, on the control voltage $V_G$ applied to the control electrode 330, the gas sensor device 300 shows the functionality of an adjustable resistor and MOSFET, respectively.

Figure 2A:
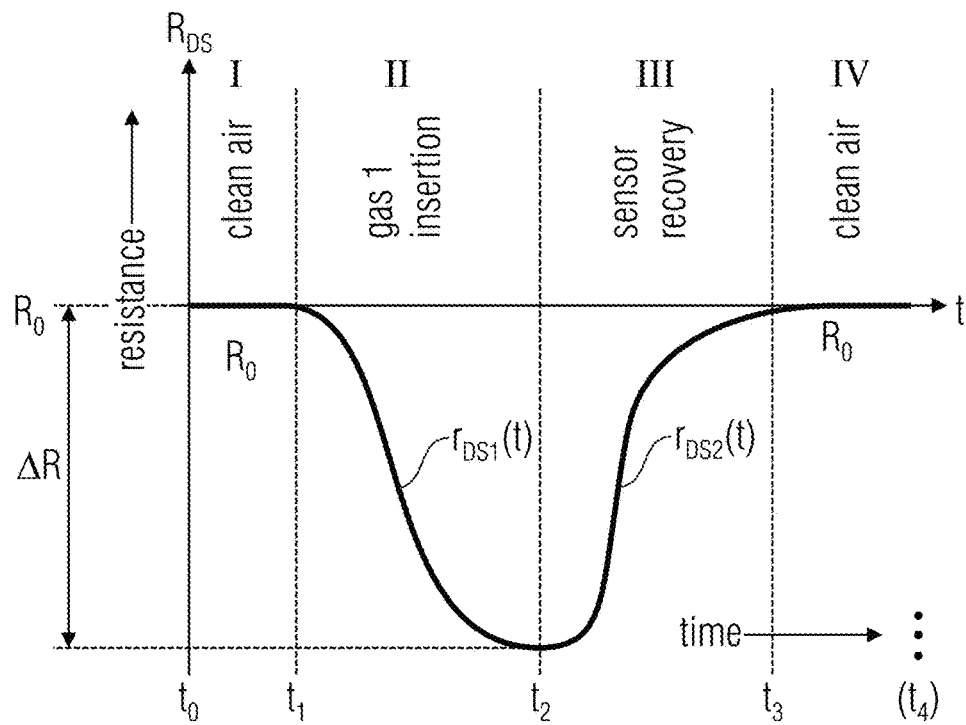
FIG. 2a shows an exemplary target gas exposure behavior of the gas sensitive material of the gas sensor device as a function of resistance values $R_{DS}$ over the time during exposure to a known target gas or target gas mixture having a known target gas or target gas mixture concentration according to an embodiment.

FIG. 2a shows an exemplary target gas exposure behavior of the gas sensitive material 310 (=sensing element) of the gas sensor device 300 as a function of resistance values $R_{DS}$ over the time t during exposure to a known target gas or target gas mixture having a known target gas or target gas mixture concentration according to an embodiment.

As described above, in step 110, the gas sensitive material 310, e.g., in form of a layer or of nanotubes, etc., of the gas sensor device 300 is exposed to different adjusted concentrations of the target gas. In step 120, the measurement values of the resistance $R_{DS}$ of the gas sensitive material 310 between the first and second contact regions 320, 322 are determined in response to the adjusted target gas concentration. To be more specific, FIG. 2a shows a typical response of the gas sensor device 300 to the target gas. For example, the sensor material may comprise graphene (Gra), or further materials, e.g., $SnO_2$/Gra, CuO/Gra, ZnO/Gra, etc. Thus, the sensor material may show a typical p-type semiconductor material behavior.

Further possible materials, usable for the gas sensitive material, may comprise, for example, graphene, graphene oxide, graphene and metal nanoparticle composites, graphene and metal oxide composites, graphene and polymer composites, metal nanowires, metal-oxide nanowires, conductive Polymer thin films or nanowires, Carbon nanotubes, etc.

The target gas may be, for example, an electron withdrawing gas, such as nitrogen dioxide ($NO_2$). Upon absorption of molecules or atoms of the target gas, e.g., an electron withdrawing target gas as $NO_2$, onto the p-type sensor material 310, the hole density of the (semiconducting) gas sensitive material 310 increases and, thus, the resistance $R_{DS}$ of the semiconducting material 310 reduces between the first and second contact regions 320, 322.

It should be noted that the above embodiment only describes one possible implementation from a plurality of different possible implementations with different sensing materials 310 which are sensitive to different target gases, respectively. Thus, depending on the used gas sensitive material, the characteristics (conduction type, resistance dependency etc. of the gas sensitive material 310 can be different or complementary to the here described exemplary embodiment(s).

The resistance $R_{DS}$ of the gas sensitive material 310 can be determined by applying a constant voltage $U_{DS}$ between the first and second contact regions 320, 322 and measuring an output signal of the gas sensor device 300, i.e., the current $I_{DS}$ between the first and second contact regions 320, 322. The output signal (output current) $I_{DS}$ is a measure for the resistance $R_{DS}$ of the gas sensitive material 310 between the first and second contact regions 320, 322.

In region I (=time interval $t_o$–$t_1$) of FIG. 2a, only clean air or a reference atmosphere (reference gas) to which the gas sensitive material 310 is essentially not sensitive, is passed over the gas sensitive material 310 of the gas sensor device 300. Thus, the resistance $R_{DS}$ corresponds to the baseline resistance $R_o$ of the gas sensitive material 310 of the gas sensor device 300.

In region II (=time interval $t_1$–$t_2$), the gas sensitive material 310 is exposed to a known concentration of the target gas, e.g., $No_2$, in the ambient atmosphere. The target gas exposure is stopped at the end of region II (at $t_2$), wherein the sensor device 300 undergoes a natural recovery in region III (=time interval $t_2$-$t_3$) under clean air (or a reference atmosphere). In region IV (=time interval $t>t_3$), the sensor device 300 should have reached its baseline $R_o$ of the resistance $R_{DS}$, with $R_{DS}=R_o$.

As indicated above with respect to step 130, the first gas sensor behavior model $R_{DS}(t)$, e.g., in form of a fitting function or a parametric model of the gas sensor behavior, is determined based on the measurement values of the resistance $R_{DS}$ of the gas sensor device 300 as a function of the adjusted target gas concentration(s). Thus, the first gas sensor behavior model $R_{DS}(t)$ is based on the dependency of the resistance $R_{DS}$ of the gas sensitive material 310 from the adjusted target gas concentration.

As is shown in FIG. 2a, the resistance $R_{DS}(t)$ can be described by the following first gas sensor behavior model (fitting function) for the timely successive regions I-IV of the sensor device exposure as shown in FIG. 2a.

First Fitting Function (First Gas Sensor Behavior Model):

| | |
|---|---|
| $R_{DS}(t) = R_o$ | in region I, |
| $R_{DS}(t) = R_o + r_{DS1}(t)$ | in region II, |
| $R_{DS}(t) = R_o + r_{DS2}(t)$ | in region III, |
| $R_{DS}(t) = R_o$ | in region IV, | wherein partial fitting functions $r_{DS1}(t)$ and $r_{DS2}(t)$ may reproduce the dependency of the resistance $R_{DS}$ of the gas sensitive material 310 in regions II and III, respectively.

The step 130 of determining the first gas sensor behavior model may be repeated for different target gas concentrations and different temperatures of the target gas and the gas sensitive material 310. Thus, the first gas sensor behavior model may cover different target gas concentrations, e.g., with 10%, 5%, 2%, 1% or 0.5% steps of changes of the target gas concentrations, and at different temperatures, e.g., with 10°, 5°, 2°, 1° or 0.5° steps of changes of the measuring temperature $T_M$.

Figure 2B:
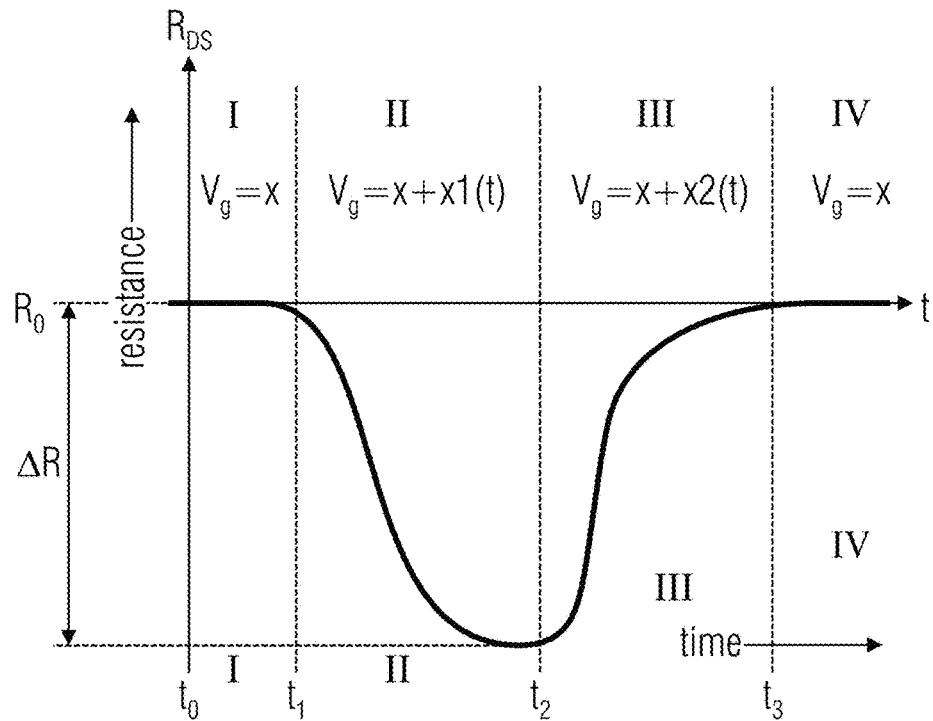
FIG. 2b shows a reproduced target gas exposure behavior of the gas sensitive material of the gas sensor device as a function a control signal applicable to a control electrode over the time by controlling the frequency (=amplitude over time) of the control signal according to an embodiment.

FIG. 2b shows an exemplary plot of a reproduced target gas exposure behavior of the gas sensitive material 310 of the gas sensor device 300 as a function a control signal $V_G$ applied (applicable) to the control electrode 330 over the time t by controlling the frequency (=amplitude over time) of the control signal (gate signal) $V_G$ according to an embodiment.

To be more specific, in step 140, the first gas sensor behavior model is translated into a corresponding second gas sensor behavior model for the resistance $R_{DS}$ of the gas sensitive material 310 of the gas sensor device 300 as a function of the control voltage (values) $V_G$ applicable to the control electrode 330, i.e., based on the dependency of the resistance $R_{DS}$ from the control voltage $V_G$.

As shown in FIG. 2b, the entire first gas sensor behavior model can be translated in the electrical domain and reproduced, i.e., the entire behavior of the gas sensor device 300 can be modeled in the electrical domain and reproduced. FIG. 2b shows an implementation of this method, wherein by controlling the frequency of the gate voltage sweep, i.e., the amplitude over the time t, the gas sensor device behavior towards the target gas, e.g., nitrogen dioxide ($NO_2$), can be reproduced. For example, this translation can be conducted for the different gas concentrations and different temperatures as described with respect to FIG. 2a.

Thus, the second gas sensor behavior model for the resistance $R_{DS}$ of the gas sensor device 300 comprises the control voltage values $V_G$ for reproducing the resistance $R_{DS}$ of the gas sensitive material 310 of the gas sensor device 300 over the time t and regions I-IV and, for example, for different target gas concentrations and/or target gas temperatures. Thus, the gas exposure behavior of the gas sensitive material 310 of the gas sensor device 300 can be reproduced by controlling the frequency (or amplitude over time) of the control voltage (gate signal). The above described concept can be extended and applied to multiple target gases or target gas mixtures.

Second Fitting Function (Second Gas Sensor Behavior Model):

| | |
|---|---|
| $V_G(t) = xo$ | in region I, |
| $V_G(t) = x_o + x1(t)$ | in region II, |
| $V_G(t) = x_o + x2(t)$ | in region III, |
| $V_G(t) = x_o$ | in region IV, | wherein partial fitting functions $x1(t)$ and $x2(t)$ may reproduce the dependency of the resistance $R_{DS}$ of the gas sensitive material 310 as function of the control voltage $V_G$ in the regions II and III, respectively.

The first fitting (function) gives a model of the sensors behavior to a particular gas. The second fitting (function) is an emulation of the sensors behavior that replicates the first fitting by using the gate voltage $V_G$ to modulate the electrical conductivity of the sensing material 310. The second fitting is empirical and several gate voltages $V_G$ are tried until the shape of the curve of the second fitting matches that of the first fitting.

Figure 3:
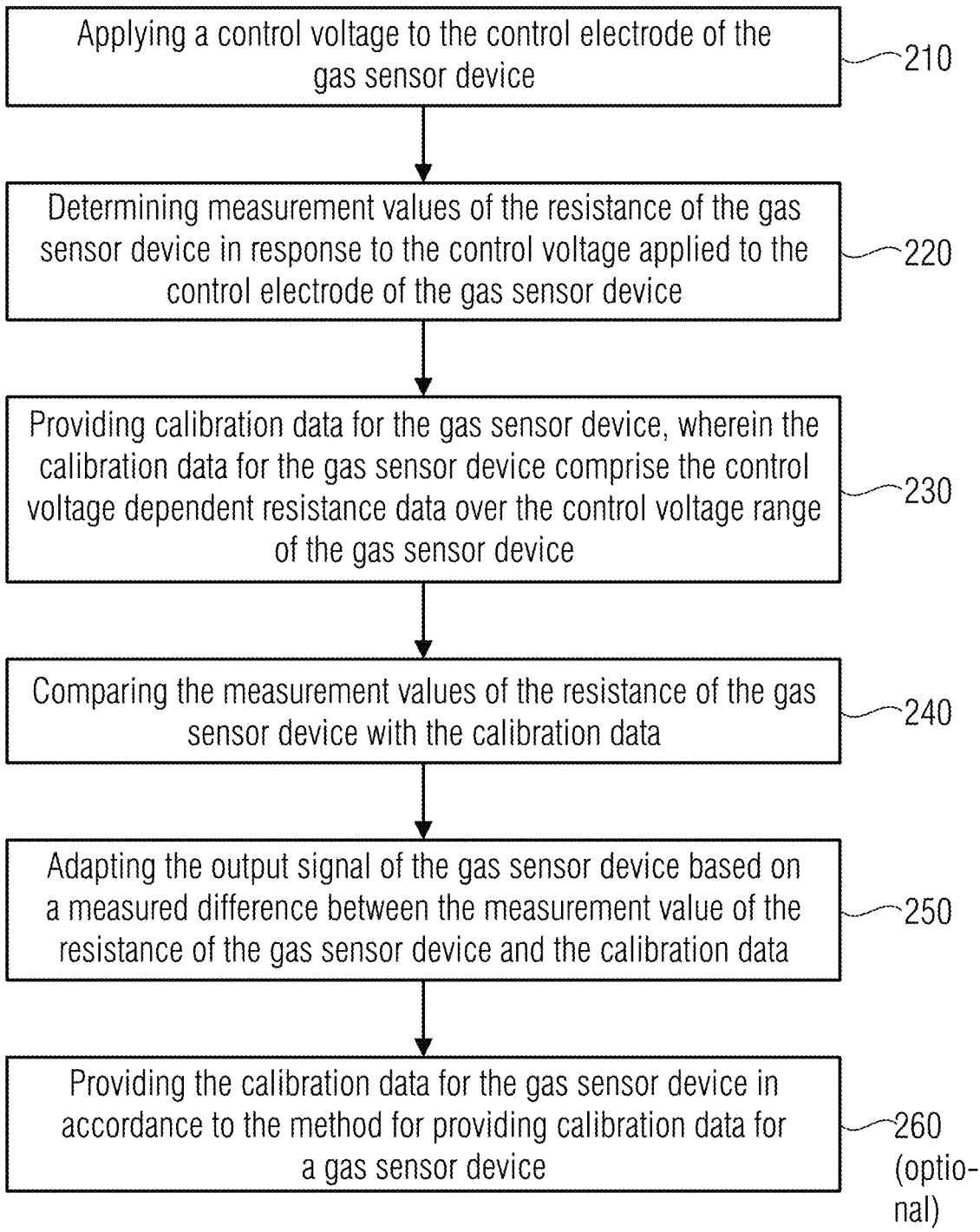
FIG. 3 shows an exemplary process flow (flowchart) of the method of calibrating or testing the gas sensor device according to an embodiment.

FIG. 3 shows an exemplary process flow (flowchart) of a method 200 of calibrating or testing the gas sensor device 300 according to an embodiment. The method 200 may be conducted on wafer level or package level during a manufacturing process of the gas sensor device 300.

According to an embodiment, the method 200 is configured to calibrate the gas sensor device 300. The gas sensor device 300 comprises a gas sensitive material 310 electrically arranged between a first and second contact region 320, 322, and a control electrode 330 which is arranged neighboring to the gas sensitive material 310, wherein the resistance $R_{DS}$ of the gas sensitive material 310 has a dependency on an environmental target gas concentration and has a dependency on a control voltage $V_G$ applicable to the control electrode. FIG. 1b shows a schematic cross sectional view of the gas sensor device 300 according to an embodiment.

In step 210 of the method 200 of calibrating the gas sensor device 300, a control voltage $V_G$ is applied to the control electrode 330 of the gas sensor device 300. In step 220 measurement values of the resistance $R_{DS}$ of the gas sensor device 300 are determined in response to the control voltage $V_G$ applied to the control electrode 330 of the gas sensor device 300.

In step 230, calibration data for the gas sensor device 300 are provided, e.g., from a memory device, wherein the calibration data for the gas sensor device 300 comprise the control voltage dependent resistance data over the control voltage range $_AV_G$ of the gas sensor device 300.

In step 240, the measurement values of the resistance $R_{DS}$ of the gas sensor device are compared with the calibration data, wherein in step 250 the output signal of the gas sensor device 300 is adapted based on a measured difference between the measurement value of the resistance $R_{DS}$ of the gas sensor device and the calibration data.

In optional step 260, the method 200 may provide the calibration data for the gas sensor device in accordance to the method 100 (see FIG. 1a) for providing calibration data for a gas sensor device 300 in accordance to a further embodiment.

According to a further embodiment, the method 200 may be further configured to conduct an automatic baseline calibration of the gas sensor device 300 based on the calibration data stored in a memory device (not shown in FIG. 1b) accessible to the gas sensor device 300.

According to a further embodiment, the step of conducting an automatic baseline calibration of the method 200 may further comprise the step of determining a control voltage dependent measurement value of the resistance $R_{DS}$ of the gas sensitive material 310 having within a tolerance range a minimum sensitivity or an insensitivity to the target gas concentration, and further the step of storing the determined control voltage dependent measurement value as the baseline calibration value $R_o$ in the memory device accessible to the gas sensor device 300, if the currently determined baseline calibration value differs from the baseline calibration value stored in the memory device. Thus, an update of the baseline calibration value may be conducted, e.g., for different temperatures $T_{M1}$, $T_{M2}$ . . . of the environmental target gas and/or the gas sensitive material.

Figure 4:
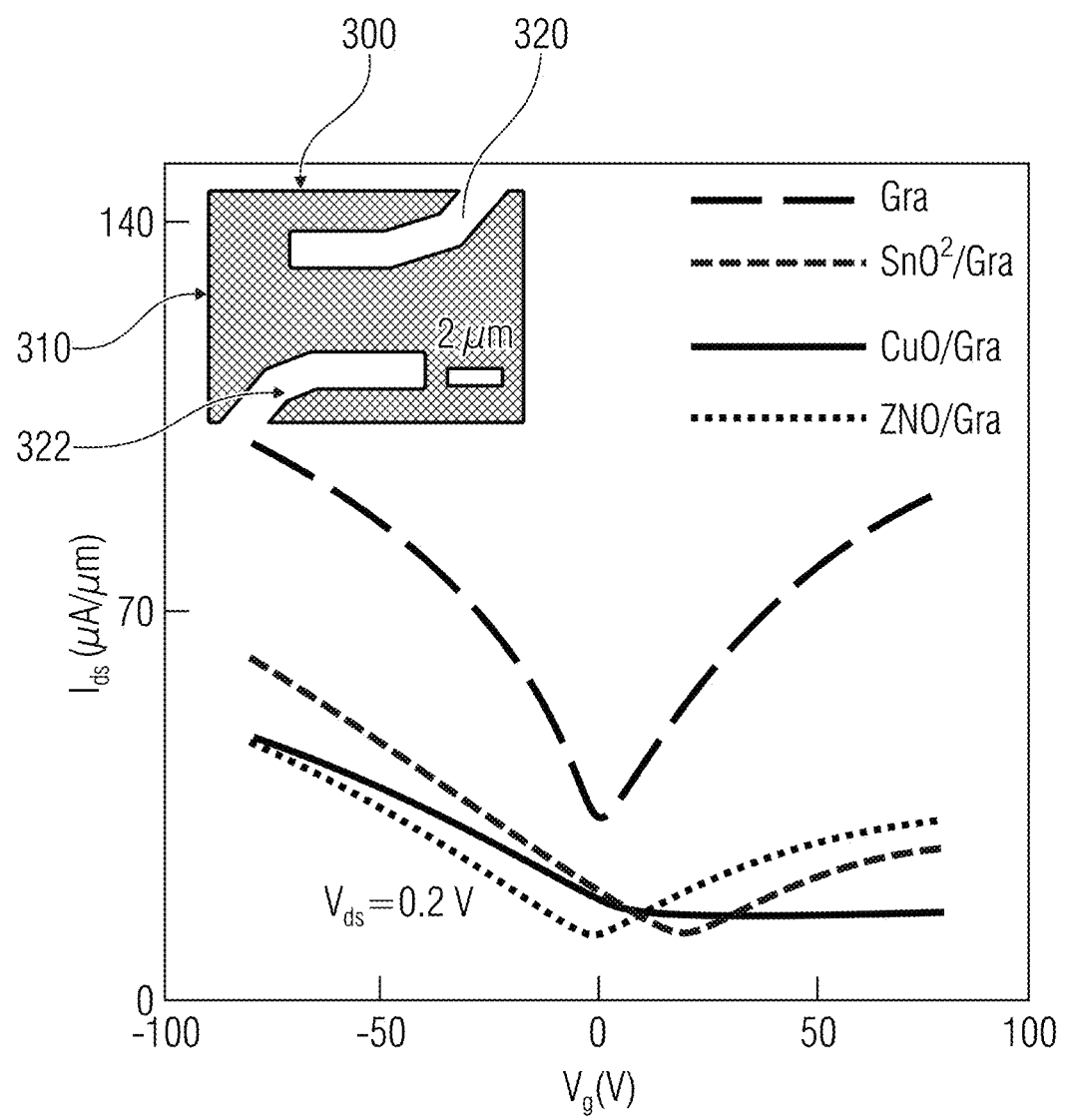
FIG. 4 shows several exemplary electrical characteristics ($I_{DS}$ vs. $V_G$ plots) of a graphene FET or graphene transistor decorated with different metal oxide nanoparticles.

For a more detailed description of the present concept for an automatic baseline calibration, FIG. 4 shows several exemplary electrical characteristics ($I_{DS}$ vs. $V_G$ plots) of a graphene FET or graphene transistor 300 decorated with different metal oxide nanoparticles as the gas sensitive material 310 (source: Zhang, Zhangyuan et al., "Hydrogen gas sensor based on metal oxide nanoparticles decorated graphene transistor", Nanoscale 7.22 (2015): 10078-10084). To be more specific, FIG. 4b shows an exemplary simplified picture of the conductivity in monolayer graphene with screen charged impurities for illustrating the Dirac regime in a graphene transistor.

The above described method 100 for providing calibration data for the gas sensor device 300 and the method 200 of calibrating the gas sensor device 300 can be used for a calibration and a final test for gas sensor devices in an inexpensive way, especially if the final use case (i.e., set of relevant gases) are constantly changing.

Embodiments of the methods 100, 200 provide an electrical emulating of the gas sensing behavior of the gas sensor device 300. This technique can also be used for in-field calibration to get and update the sensor baseline $R_o$. Thus, the methods 100, 200 can be extended to in-field automatic baseline calibration to compensate for $R_o$ drift or sensor poisoning. FIG. 4 demonstrates how the behavior of the "$I_{DS}$ vs. $V_G$" change with changing the gas sensitive material 310, e.g., the graphene composite (=functionalization). In the case of FIG. 4, a CuO/graphene material demonstrates a typical p-type semiconductor behavior, i.e., the device is completely off during the application of a positive $V_G$ ($V_G$>0V). Thus no amount of additional +ve doping (ve=electron charges) from the target gas molecules will influence the gas sensor device 300. Whereas a gas molecule with a negative doping might have an effect, which can be counteracting by increasing $V_G$. This will shift the "dirac point". Moreover, the "conductance vs. $V_G$ characteristics" of the gas sensitive material 310 change with temperature. Moreover, the drain-source current $I_{DS}$ may change versus the gate voltage $V_G$ under certain gas concentration conditions.

By knowing the "dirac point" at which the gas sensing material 310 is completely insensitive or has a minimum sensitivity to ambient gases or gases of interest, an automatic baseline $R_o$ correction can be carried out and a baseline $R_o$ can be obtained, which can be used to over-write or compensate the stored $R_o$ value baseline. The baseline $R_o$ is the output value, when the gas sensor device 300 is not exposed to a stimulus, i.e., a target gas. Theoretically, for a gas sensor device 300 with no drift, the baseline $R_o$ should remain constant. Practically, gas sensor devices 300 show a drift of the baseline $R_o$ over time, however.

It should be noted that the "dirac point" is influenced by the functionalization (the gas sensitive material 310), the (target) gas concentration and/or temperature. By using one or all of the parameters the regime at which the gas sensor devices are insensitive or have a minimum sensitivity to ambient gases can be identified and, thus, can used for automatic baseline correction. The dirac point of the sensor element can be determined from the local minimum of the drain-source current $I_{DS}$ versus the gate voltage $V_G$.

In the present concept of baseline calibration, the gate bias $V_G$ is swept or tuned between the switch-on state and the switch-off state of the sensitivity of the gas sensor device 300 in order to determine the baseline resistance $R_o$, i.e., to determine the minimum of the drain source current $I_{DS}$ versus the gate voltage $V_G$ obtained during this process, and to compare the obtained baseline resistance $R_o$ with the expected value for the baseline resistance $R_o$. If a difference occurs between the current baseline resistance $R_o$ and the previously stored baseline resistance $R'_o$, an automatic correction of the baseline resistance $R_o$ can be performed in order to compensate and correct, respectively, a corresponding e.g., age-related, drift of the output signal of the gas sensor device 300 and hence the baseline resistance $R_o$ value. Thus, the value $_\Delta R_o$ between the current baseline resistance $R_o$ and the previously stored baseline resistance $R'_o$, is determined.

According to embodiments, the sensor material is not limited to graph materials, wherein any resistive materials depending on the gas concentration to be detected can be used.

Figure 5:
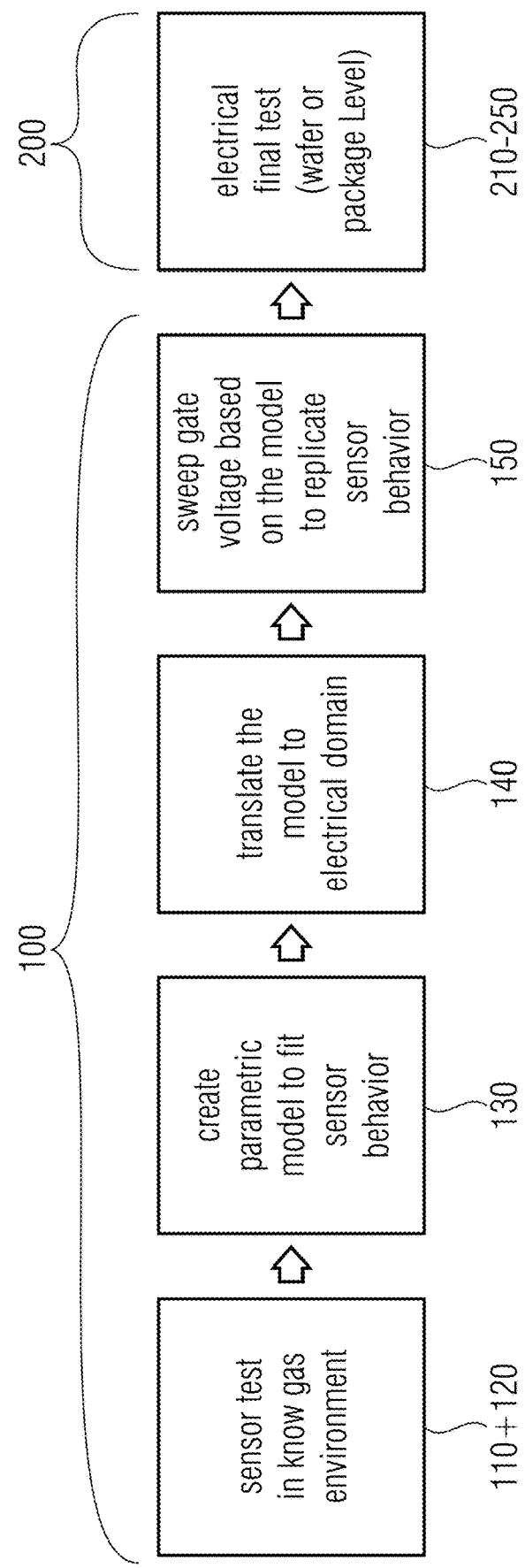
FIG. 5 shows a summary of the exemplary process flow of the method of calibrating or testing the gas sensor device according to an embodiment.

FIG. 5 shows a summary of the exemplary process flow (flowchart) of the method 100 for providing calibration data for a gas sensor device 300 according and the method 200 of calibrating or testing the gas sensor device 300 according to an embodiment.

Steps 110 and 120 of method 100 can be summarized as sensor test in a known gas environment. Step 130 of method 100 can be summarized as a creation of a parametric model to fit the sensor behavior. Step 140 of method 100 can be summarized as a translation of the model (the first gas sensor behavior model) to the electrical domain. Step 150 of method 100 can be summarized as sweeping the gate voltage (control voltage) $V_G$ based on the (sensor behavior) model to replicate sensor behavior. The steps of method 200 can be summarized as electrical final test (on waver or a package level).

The methods 100/200 can be repeated for several different concentrations and gases. By running more than one gate sweep (multiple concentrations), calibration data for the gas sensor device 300 can be extracted. This calibration data can then be stored on the sensor chip (ASIC), as shown in FIG. 6a below.

Figure 6A:
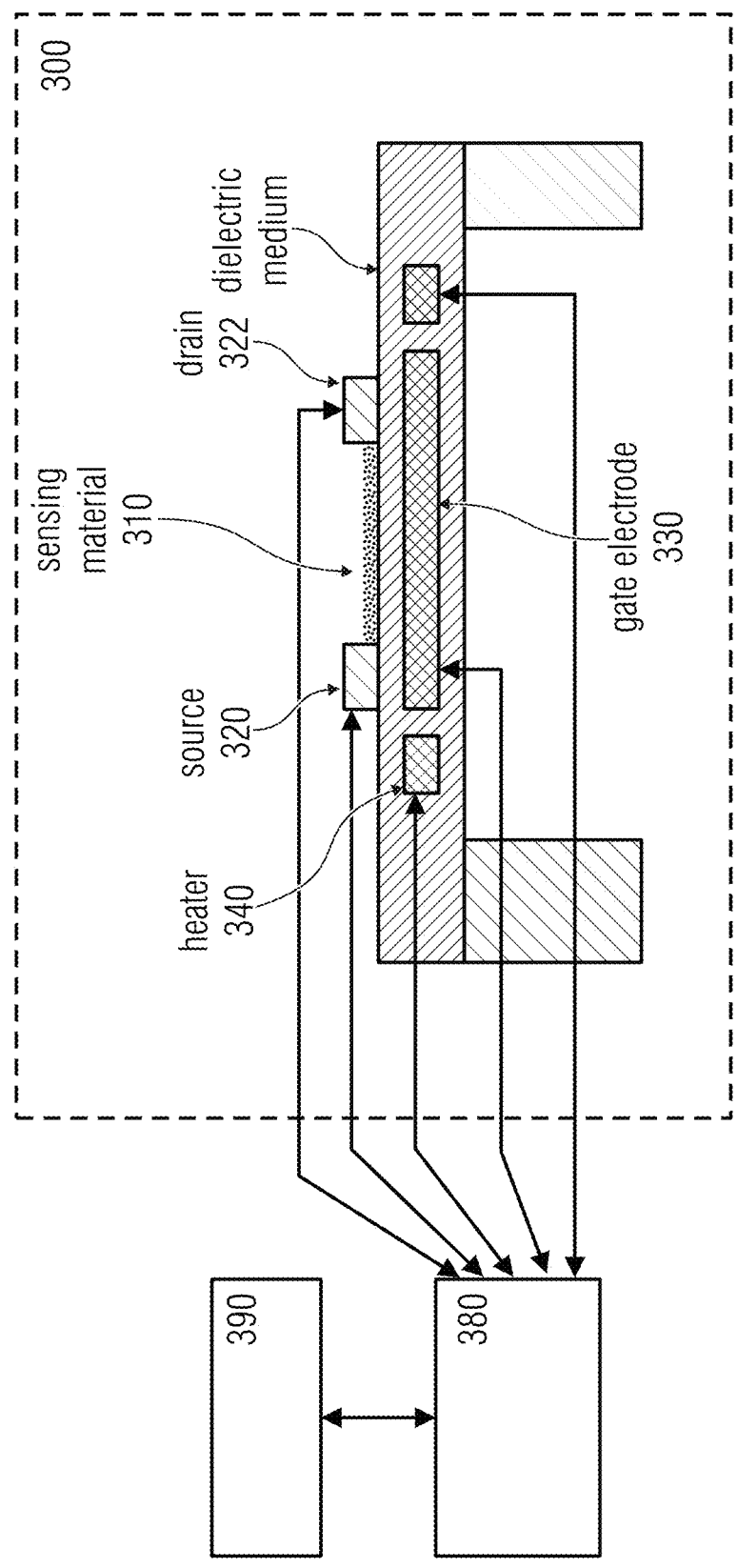
FIG. 6a shows a schematic illustration of a gas sensor arrangement having a gas sensor device connected to a processing device according to an embodiment.

FIG. 6a shows a schematic illustration of a gas sensor arrangement 400 having a gas sensor device 300 connected to a processing device 380 according to an embodiment. FIG. 6a further shows a schematic cross sectional view of a gas sensor device 300 (see also FIG. 1b) connected to a processing device 380 for providing calibration data.

As shown in FIG. 6a, the gas sensor device 300 comprises a gas sensitive material 310 electrically arranged between a first and second contact region (or contact pad) 320, 322, and a control electrode 330 which is arranged neighboring to the gas sensitive material 310. The resistance RDS of the gas sensitive material 310 has a dependency on an environmental target gas concentration and has a dependency on a control voltage VG applicable to the control electrode 330. As shown in FIG. 6a, the gas sensor device 300 may further comprise a heating element 340 neighboring to the gas sensitive material 310 for heating the environmental target gas and/or the gas sensitive material to a further measuring temperature TM1.

According to an embodiment, the processing device 380 may be implemented as an on-chip ASIC (ASIC=application specific integrated circuit) of the gas sensor device 300. According to a further embodiment, the processing device 380 may also be implemented as an external processing device, e.g., external to the gas sensor device 300.

The processing device 380 of FIG. 6a for the gas sensor device 300 may be configured to conduct the steps of the method 100 as shown in FIG. 1, for example.

To be more specific, the processing device 380 is configured to determine measurement values of the resistance $R_{DS}$ of the gas sensitive material 310 in response to the adjusted target gas concentration, during exposing the gas sensitive material 310 of the gas sensor device 300, e.g., during the test period, to an adjusted target gas concentration. The processing device 380 is further configured to determine a first gas sensor behavior model based on the measurement values of the resistance of the gas sensitive material as a function of the adjusted target gas concentration. The processing device 380 is further configured to translate the first gas sensor behavior model into a corresponding second gas sensor behavior model for the resistance $R_{DS}$ of the gas sensitive material 310 as a function of the control voltage applicable to the control electrode 330.

The processing device 380 is further configured to sweep the control voltage $V_G$ based on the second gas sensor behavior model over a control voltage range $_\Delta V_G$ for providing the control voltage dependent resistance data, wherein the provided control voltage dependent resistance data over the control voltage range $_\Delta V_G$ of the gas sensor device 300 or data derived therefrom form the calibration data for the gas sensor device 300.

According to an embodiment, different values of the control voltage over the control voltage range $_\Delta V_G$ correspond to different target gas concentrations at a measuring temperature $T_M$.

The gas sensor device 300 may further comprise at least one heating element 340 neighboring to the gas sensitive material 310, wherein the processing device 380 is further configured to activate the heating element 340 for heating the environmental target gas and/or the gas sensitive material to a further measuring temperature $T_{M1}$, and to determine the control voltage dependent resistance data over the control voltage range $_\Delta V_G$ also for the further measuring temperature.

According to an embodiment, the processing device 380 is further configured to store the calibration data on a memory device 390 which is accessible to the processing device 380 and/or the gas sensor device 300.

According to an embodiment, the processing device 380 is further configured to determine the measurement values of the resistance of the gas sensitive material 310 for different target gas concentrations and/or for different target gas compositions.

According to an embodiment, the control voltage dependent resistance data of the gas sensor device 300 depend on the frequency and/or the amplitude of the control voltage $V_G$.

According to an embodiment, the processing device 380 is further configured to determine a control voltage dependent measurement value of the resistance $R_{DS}$ of the gas sensitive material 310 having within a tolerance range an insensitivity to the target gas concentration, and to store the determined control voltage dependent measurement value as the baseline calibration value $R_o$ in the memory device 380 accessible to the gas sensor device 300 and/or to the processing device 380.

According to an embodiment, the processing device 380 is further configured to determine the control voltage dependent measurement value of the resistance $R_{DS}$ of the gas sensitive material 310 having a complete insensitivity to the target gas concentration for different temperatures of the environmental target gas and/or the gas sensitive material, and to store the determined control voltage dependent measurement value as the baseline calibration value $R_o$ in the memory device 390 accessible to the gas sensor device 300 and/or to the processing device 380, wherein the baseline calibration value $R_o$ is also independent of the temperature $T_M$ of the environmental target gas and/or the gas sensitive material 310 exposed to the target gas.

The processing device 380 of FIG. 6a for the gas sensor device 300 may also be configured to conduct the steps of the method 300 for calibrating the gas sensor device, e.g., on wafer level or package level, as shown in FIG. 3, for example.

To be more specific, the processing device 380 is configured to apply a control voltage $V_G$ to the control electrode 330 of the gas sensor device 300, and to determine measurement values of the resistance $R_{DS}$ of the gas sensor device 300 in response to the control voltage $V_G$ applied to the control electrode 330 of the gas sensor device 300.

The processing device 380 is further configured to provide calibration data for the gas sensor device 300, wherein the calibration data for the gas sensor device 300 comprise the control voltage dependent resistance data over the control voltage range $_\Delta V_G$ of the gas sensor device 300, and to compare the measurement values of the resistance $R_{DS}$ of the gas sensor device 300 with calibration data, e.g. stored in a memory device 390.

The processing device 380 is further configured to adapt the output signal of the gas sensor device 300 based on a measured difference between the measurement value of the resistance $R_{DS}$ of the gas sensor device 300 and the calibration data.

According to an embodiment, the processing device 380 for calibrating the gas sensor device 300 is further configured for providing the calibration data according the method 100.

The processing device 380 is further configured to conduct an automatic baseline calibration of the gas sensor device 300 based on the calibration data stored in a memory device 390 accessible to the gas sensor device 300 and/or to the processing device 380.

The processing device 380 is further configured to conduct an automatic baseline calibration further by determining a control voltage dependent measurement value of the resistance $R_{DS}$ of the gas sensitive material 310 having a minimum sensitivity or complete insensitivity to the target gas concentration, and by storing the determined control voltage dependent measurement value as the baseline calibration value $R_o$ in the memory device 390 accessible to the gas sensor device 300 and/or to the processing device 380, if the currently determined baseline calibration value $R'_o$ differs from the baseline calibration value $R_o$ stored in the memory device 390. Thus, an update of the baseline calibration value may be conducted, e.g., for different temperatures $T_{M1}, T_{M2} \ldots$ of the environmental target gas and/or the gas sensitive material.

Figure 6B:
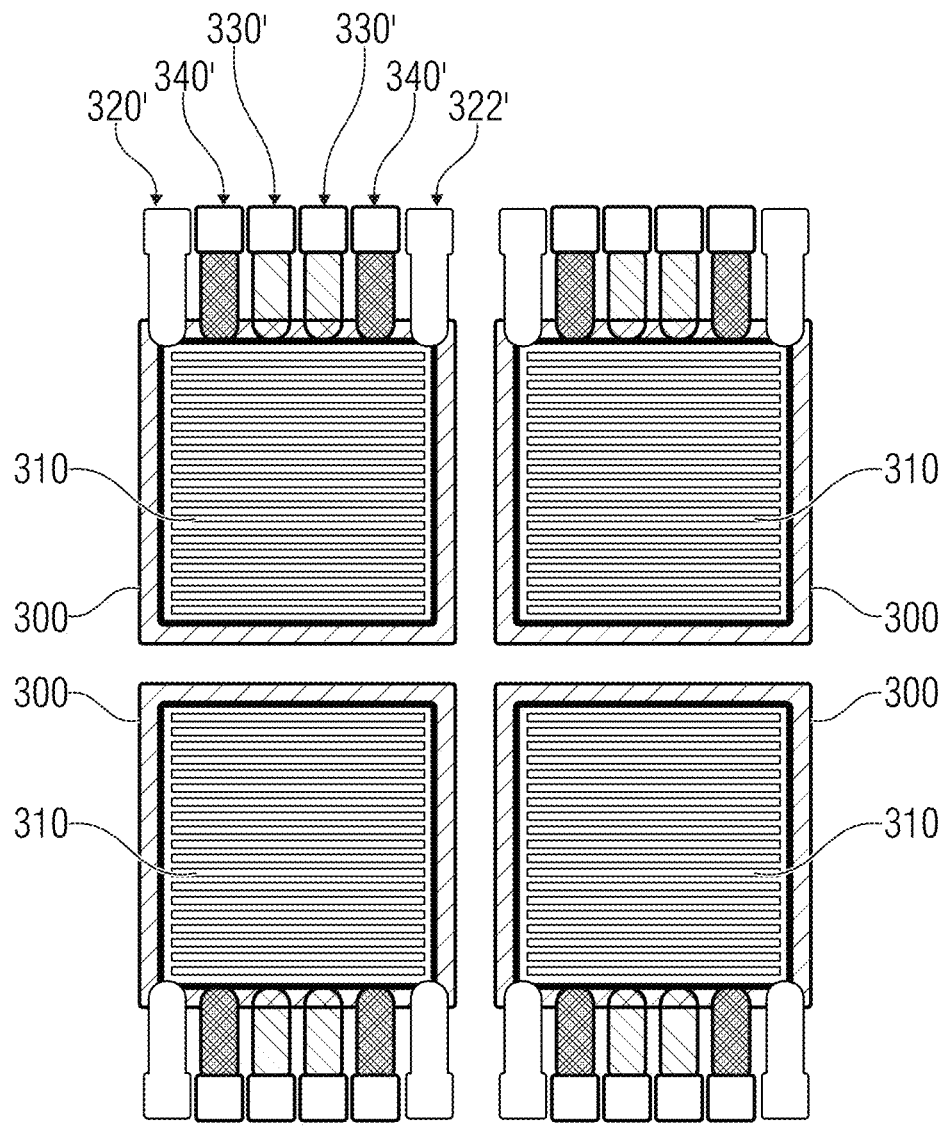
FIG. 6b shows a schematic exemplary plane view of a gas sensor device having a four sensor array configuration according to an embodiment.

FIG. 6b shows a schematic exemplary plane view of a gas sensor arrangement 400 having a four (or "n") sensor array configuration, i.e. four (or n with n=2, 3, 4, 5 . . . ) gas sensor devices 300, according to an embodiment. The "n" gas sensor devices 300 of FIG. 6b may comprise the structure and the dimensions of the gas sensor device 300 of FIG. 1b or 6a.

As shown in FIG. 6b, the contact pad 320' may be connected to the first contact region (source) 320, the contact pad 322' may be connected to the second contact region (source) 322, the contact pads 340' may be connected to the heating element(s) 340, and the contact pad 330' may be connected to the control electrode (gate) 330.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

Additional embodiments and aspects are described which may be used alone or in combination with the features and functionalities described herein.

One embodiment provides a method for providing calibration data for a gas sensor device, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, the method comprising: exposing the gas sensitive material of the gas sensor device to different adjusted target gas concentrations of a target gas, determining measurement values of the resistance of the gas sensitive material between the first and second contact region in response to the adjusted target gas concentration, determining a first gas sensor behavior model based on the measurement values of the resistance of the gas sensitive material of the gas sensor device as a function of the adjusted target gas concentration, translating the first gas sensor behavior model into a corresponding second gas sensor behavior model for the resistance of the gas sensitive material of the gas sensor device as a function of the control voltage applicable to the control electrode, and sweeping the control voltage based on the second gas sensor behavior model over a control voltage range for providing control voltage dependent resistance data, wherein the provided control voltage dependent resistance data or data derived therefrom over the control voltage range of the gas sensor device form the calibration data for the gas sensor device.

According to one aspect, different values of the control voltage over the control voltage range correspond to different target gas concentrations at a measuring temperature.

According to another aspect, the gas sensor device further comprises a heating element neighboring to the gas sensitive material, the method further comprising: activating the heating element for heating the environmental target gas and/or the gas sensitive material to a further measuring temperature, and additionally conducting the steps of exposing the gas sensor device, determining measurement values, determining a first gas sensor behavior model, translating the first gas sensor behavior model into a second gas sensor behavior model, and sweeping the control voltage for the further measuring temperature $T_{M1}$, and determining the control voltage dependent resistance data over the control voltage range also for the further measuring temperature.

According to another aspect, the method further comprises: storing the calibration data on a memory device which is accessible to the processing device.

According to another aspect, the method further comprises: repeating the step of determining measurement values of the resistance of the gas sensitive material for different target gas concentrations and/or for different target gas compositions.

According to another aspect, the control voltage dependent resistance data of the gas sensor device depend on the frequency and/or the amplitude of the control voltage.

According to another aspect, the method further comprises: determining a control voltage dependent measurement value of the resistance of the gas sensitive material having within a tolerance range an insensitivity to the target gas concentration, and storing the determined control voltage dependent measurement value as a baseline calibration value in the memory device accessible to the processing device.

According to another aspect, the method further comprises: determining the control voltage dependent measurement value of the resistance of the gas sensitive material having a complete insensitivity to the target gas concentration for different temperatures of the environmental target gas and/or of the gas sensitive material, and storing the determined control voltage dependent measurement value as the baseline calibration value in a memory device accessible to the processing device, wherein the baseline calibration value is also independent of the temperature of the environmental target gas and/or the gas sensitive material exposed to the target gas.

Another embodiment provides a method of calibrating a gas sensor device, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, the method comprising: applying a control voltage to the control electrode of the gas sensor device, determining measurement values of the resistance of the gas sensor device in response to the control voltage applied to the control electrode of the gas sensor device, providing calibration data for the gas sensor device, wherein the calibration data for the gas sensor device comprise the control voltage dependent resistance data over the control voltage range of the gas sensor device, comparing the measurement values of the resistance of the gas sensor device with the calibration data, and adapting the output signal of the gas sensor device based on a measured difference between the measurement value of the resistance of the gas sensor device and the calibration data.

According to one aspect, the method further comprises: providing the calibration data for the gas sensor device in accordance to the above method for providing calibration data for a gas sensor device.

According to another aspect, the method further comprises: conducting an automatic baseline calibration of the gas sensor device based on the calibration data stored in a memory device accessible to the processing device.

According to another aspect, conducting an automatic baseline calibration further comprises: determining a control voltage dependent measurement value of the resistance of the gas sensitive material having within a tolerance range an insensitivity to the target gas concentration, and storing the determined control voltage dependent measurement value as the baseline calibration value in the memory device accessible to the processing device, if the currently determined baseline calibration value differs from the baseline calibration value stored in the memory device.

Another embodiment provides a processing device for a gas sensor device for providing calibration data, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, wherein the processing device is configured to: determine measurement values of the resistance of the gas sensitive material in response to the adjusted target gas concentration, during exposing the gas sensitive material of the gas sensor device to an adjusted target gas concentration, determine a first gas sensor behavior model based on the measurement values of the resistance of the gas sensitive material as a function of the adjusted target gas concentration, to translate the first gas sensor behavior model into a corresponding second gas sensor behavior model for the resistance of the gas sensitive material as a function of the control voltage applicable to the control electrode, and to sweep the control voltage based on the second gas sensor behavior model over a control voltage range for providing the control voltage dependent resistance data, wherein the provided control voltage dependent resistance data over the control voltage range of the gas sensor device or data derived therefrom form the calibration data for the gas sensor device.

According to one aspect, different values of the control voltage over the control voltage range correspond to different target gas concentrations at a measuring temperature.

According to another aspect, the gas sensor device further comprises a heating element neighboring to the gas sensitive material, wherein the processing device is further configured to: activate the heating element for heating the environmental target gas and/or the gas sensitive material to a further measuring temperature, and determine the control voltage dependent resistance data over the control voltage range also for the further measuring temperature.

According to another aspect, the processing device is further configured to: store the calibration data on a memory device which is accessible to the processing device.

According to another aspect, the processing device is further configured to: determine the measurement values of the resistance of the gas sensitive material for different target gas concentrations and/or for different target gas compositions.

According to another aspect, the control voltage dependent resistance data of the gas sensor device depend on the frequency and/or the amplitude of the control voltage.

According to another aspect, the processing device is further configured to: determine a control voltage dependent measurement value of the resistance of the gas sensitive material having within a tolerance range an insensitivity to the target gas concentration, and store the determined control voltage dependent measurement value as the baseline calibration value in the memory device accessible to the processing device.

According to another aspect, the processing device is further configured to: determine the control voltage dependent measurement value of the resistance of the gas sensitive material having a complete insensitivity to the target gas concentration for different temperatures of the environmental target gas and/or the gas sensitive material, and store the determined control voltage dependent measurement value as the baseline calibration value in the memory device accessible to the processing device, wherein the baseline calibration value is also independent of the temperature of the environmental target gas and/or the gas sensitive material exposed to the target gas.

Another embodiment provides a processing device for calibrating a gas sensor device, wherein the gas sensor device comprises a gas sensitive material electrically arranged between a first and second contact region, and a control electrode which is arranged neighboring to the gas sensitive material, wherein the resistance of the gas sensitive material has a dependency on an environmental target gas concentration and has a dependency on a control voltage applicable to the control electrode, wherein the processing device is configured to: apply a control voltage to the control electrode of the gas sensor device, determine measurement values of the resistance of the gas sensor device in response to the control voltage applied to the control electrode of the gas sensor device, provide calibration data for the gas sensor device, wherein the calibration data for the gas sensor device comprise the control voltage dependent resistance data over the control voltage range of the gas sensor device, compare the measurement values of the resistance of the gas sensor device with associated calibration data, and adapt the output signal of the gas sensor device based on a measured difference between the measurement value of the resistance of the gas sensor device and the associated calibration data.

According to one aspect, the processing device for calibrating a gas sensor device further comprises the above processing device for a gas sensor device for providing calibration data.

According to another aspect, the processing device according is further configured to: conduct an automatic baseline calibration of the gas sensor device based on the calibration data stored in the memory device accessible to the processing device.

According to another aspect, the processing device according is further configured to: conduct an automatic baseline calibration further by determining a control voltage dependent measurement value of the resistance of the gas sensitive material having a complete insensitivity to the target gas concentration, and storing the determined control voltage dependent measurement value as the baseline calibration value in the memory device accessible to the processing device, if the currently determined baseline calibration value differs from the baseline calibration value stored in the memory device.

Depending on certain implementation requirements, embodiments of the processing device can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable. Some embodiments comprise a data carrier having electronically readable control signals, which are capable of cooperating with a programmable computer system, such that one of the methods described herein is performed.

Generally, embodiments of the processing device can be implemented as a computer program product with a program code, the program code being operative for performing one of the methods when the computer program product runs on a computer. The program code may for example be stored on a machine readable carrier. Other embodiments comprise the computer program for performing one of the methods described herein, stored on a machine readable carrier. In other words, an embodiment of the method is, therefore, a computer program having a program code for performing one of the methods described herein, when the computer program runs on a computer.

A further embodiment of the methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory. A further embodiment comprises a processing means, for example a computer, or a programmable logic device, configured to or adapted to perform one of the methods described herein. A further embodiment comprises a computer having installed thereon the computer program for performing one of the methods described herein.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer. The methods described herein may be performed using a hardware apparatus, or using a computer, or using a combination of a hardware apparatus and a computer.

In the foregoing Detailed Description, it can be seen that various features are grouped together in examples for the purpose of streamlining the disclosure. This method of disclosure is not to be interpreted as reflecting an intention that the claimed examples require more features than are expressly recited in each claim. Rather, as the following claims reflect, subject matter may lie in less than all features of a single disclosed example. Thus the following claims are hereby incorporated into the Detailed Description, where each claim may stand on its own as a separate example. While each claim may stand on its own as a separate example, it is to be noted that, although a dependent claim may refer in the claims to a specific combination with one or more other claims, other examples may also include a combination of the dependent claim with the subject matter of each other dependent claim or a combination of each feature with other dependent or independent claims. Such combinations are proposed herein unless it is stated that a specific combination is not intended. Furthermore, it is intended to include also features of a claim to any other independent claim even if this claim is not directly made dependent to the independent claim.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that the embodiments be limited only by the claims and the equivalents thereof.

What is claimed is:

1. A method for providing calibration data for a gas sensor device,
wherein the gas sensor device comprises a gas sensitive material electrically arranged between a first and second contact region, and a control electrode which is arranged neighboring to the gas sensitive material, wherein a resistance of the gas sensitive material has a dependency on an environmental target gas concentration and has a dependency on a control voltage applicable to the control electrode,
the method comprising:
exposing the gas sensitive material of the gas sensor device to different adjusted target gas concentrations of a target gas;
determining measurement values of the resistance of the gas sensitive material between the first and second contact region in response to the adjusted target gas concentration;
determining a first gas sensor behavior model based on the measurement values of the resistance of the gas sensitive material as a function of the adjusted target gas concentration, wherein the first gas sensor behavior model comprises a first fitting function comprising a first partial fitting function corresponding only to a gas insertion phase and a second fitting function comprising a second partial fitting function corresponding only to a natural recovery phase, wherein the gas insertion phase and the natural recovery phase comprise non-overlapping time intervals;
translating the first gas sensor behavior model into a corresponding second gas sensor behavior model for the resistance of the gas sensitive material of the gas sensor device as a function of the control voltage applicable to the control electrode, wherein the second gas sensor behavior model comprises a second fitting function comprising a first partial fitting function corresponding only to the gas insertion phase and a second fitting function comprising a second partial fitting function corresponding only to the natural recovery phase;
sweeping the control voltage based on the second gas sensor behavior model over a control voltage range for providing control voltage dependent resistance data, wherein the provided control voltage dependent resistance data or data derived therefrom over a control voltage range of the gas sensor device form the calibration data for the gas sensor device;
determining, for different temperatures of at least one of the environmental target gas or the gas sensitive material, a control voltage dependent measurement value of the resistance of the gas sensitive material having, within a tolerance range, an insensitivity to the target gas concentration; and
storing the determined control voltage dependent measurement value as a baseline calibration value in a memory device accessible to a processing device, wherein the baseline calibration value is also independent of the temperature of at least one of the environmental target gas or the gas sensitive material exposed to the target gas.

2. The method according to claim 1, wherein different values of the control voltage over the control voltage range correspond to different target gas concentrations at a measuring temperature.

3. The method according to claim 1, wherein the gas sensor device further comprises a heating element neighboring to the gas sensitive material, the method further comprising:
activating the heating element for heating the environmental target gas and/or the gas sensitive material to a further measuring temperature; and
additionally conducting the steps of exposing the gas sensor device, determining measurement values, determining the first gas sensor behavior model, translating the first gas sensor behavior model into a second gas sensor behavior model, and sweeping the control voltage for the further measuring temperature; and
determining the control voltage dependent resistance data over the control voltage range also for the further measuring temperature.

4. The method according to claim 1, further comprising:
storing the calibration data on the memory device which is accessible to the processing device.

5. The method according to claim 1, further comprising:
repeating the step of determining measurement values of the resistance of the gas sensitive material for different target gas concentrations and/or for different target gas compositions.

6. The method according to claim 1, wherein the control voltage dependent resistance data of the gas sensor device depend on a frequency and/or an amplitude of the control voltage.

7. A method of calibrating a gas sensor device,
wherein the gas sensor device comprises a gas sensitive material electrically arranged between a first and second contact region, and a control electrode which is arranged neighboring to the gas sensitive material, wherein a resistance of the gas sensitive material has a dependency on an environmental target gas concentration and has a dependency on a control voltage applicable to the control electrode,
the method comprising:
applying the control voltage to the control electrode of the gas sensor device;
determining measurement values of the resistance of the gas sensor device in response to the control voltage applied to the control electrode of the gas sensor device during a first clean air phase, a gas insertion phase, a natural recovery phase, and a second clean air phase, wherein the gas insertion phase and the natural recovery phase comprise non-overlapping time intervals;
determining a first gas sensor behavior model based on the measurement values wherein the first gas sensor behavior model comprises a first fitting function comprising a first partial fitting function corresponding only to the gas insertion phase and a second fitting function comprising a second partial fitting function corresponding only to the natural recovery phase;
providing calibration data for the gas sensor device, wherein the calibration data for the gas sensor device is derived from control voltage dependent resistance data over a control voltage range of the gas sensor device;
determining a second gas sensor behavior model based on the calibration wherein the second gas sensor behavior model comprises a second fitting function comprising a first partial fitting function corresponding only to the gas insertion phase and a second fitting function comprising a second partial fitting function corresponding only to the natural recovery phase;
comparing the measurement values of the resistance of the gas sensor device with the calibration data;
adapting, using the first and second gas sensor behavior models, an output signal of the gas sensor device based on a measured difference between the measurement values of the resistance of the gas sensor device and the calibration data;
determining, for different temperatures of at least one of the environmental target gas or the gas sensitive material, a control voltage dependent measurement value of the resistance of the gas sensitive material having within a tolerance range an insensitivity to the target gas concentration; and
storing the determined control voltage dependent measurement value as a baseline calibration value in a memory device accessible to a processing device if a currently determined baseline calibration value differs from the baseline calibration value stored in the memory device, wherein the baseline calibration value is also independent of the temperature of at least one of the environmental target gas or the gas sensitive material exposed to the target gas.

8. The method according to claim 7, further comprising:
conducting an automatic baseline calibration of the gas sensor device based on the calibration data stored in the memory device accessible to the processing device.

9. A processing device for a gas sensor device for providing calibration data,
wherein the gas sensor device comprises a gas sensitive material electrically arranged between a first and second contact region, and a control electrode which is arranged neighboring to the gas sensitive material, wherein a resistance of the gas sensitive material has a dependency on an environmental target gas concentration and has a dependency on a control voltage applicable to the control electrode,
wherein the processing device is configured to:
determine measurement values of the resistance of the gas sensitive material in response to an adjusted target gas concentration, during exposing the gas sensitive material of the gas sensor device to the adjusted target gas concentration;
determine a first gas sensor behavior model based on the measurement values of the resistance of the gas sensitive material as a function of the adjusted target gas concentration, wherein the first gas sensor behavior model comprises a first fitting function comprising a first partial fitting function corresponding only to a gas insertion phase and a second fitting function comprising a second partial fitting function corresponding only to a natural recovery phase, wherein the gas insertion phase and the natural recovery phase comprise non-overlapping time intervals;
translate the first gas sensor behavior model into a corresponding second gas sensor behavior model for the resistance of the gas sensitive material as a function of the control voltage applicable to the control electrode, wherein the second gas sensor behavior model comprises a second fitting function comprising a first partial fitting function corresponding only to the gas insertion phase and a second fitting function comprising a second partial fitting function corresponding only to the natural recovery phase;

sweep the control voltage based on the second gas sensor behavior model over a control voltage range for providing control voltage dependent resistance data, wherein the provided control voltage dependent resistance data over a control voltage range of the gas sensor device or data derived therefrom form the calibration data for the gas sensor device;

determine a control voltage dependent measurement value of the resistance of the gas sensitive material having a complete insensitivity to the target gas concentration for different temperatures of at least one of the environmental target gas or the gas sensitive material; and store the determined control voltage dependent measurement value as a baseline calibration value in a memory device accessible to the processing device, wherein the baseline calibration value is also independent of the temperature of at least one of the environmental target gas or the gas sensitive material exposed to the target gas.

10. The processing device according to claim 9, wherein different values of the control voltage over the control voltage range correspond to different target gas concentrations at a measuring temperature.

11. The processing device according to claim 9, wherein the gas sensor device further comprises a heating element neighboring to the gas sensitive material,
wherein the processing device is further configured to:
activate the heating element for heating the environmental target gas and/or the gas sensitive material to a further measuring temperature; and
determine the control voltage dependent resistance data over a control voltage range also for the further measuring temperature.

12. The processing device according to claim 9, further configured to:
store the calibration data on the memory device which is accessible to the processing device.

13. The processing device according to claim 9, further configured to:
determine the measurement values of the resistance of the gas sensitive material for different target gas concentrations and/or for different target gas compositions.

14. The processing device according to claim 9, wherein the control voltage dependent resistance data of the gas sensor device depend on a frequency and/or an amplitude of the control voltage.

15. A processing device for calibrating a gas sensor device,
wherein the gas sensor device comprises a gas sensitive material electrically arranged between a first and second contact region, and a control electrode which is arranged neighboring to the gas sensitive material, wherein a resistance of the gas sensitive material has a dependency on an environmental target gas concentration and has a dependency on a control voltage applicable to the control electrode, wherein the processing device is configured to:
apply the control voltage to the control electrode of the gas sensor device;
determine measurement values of the resistance of the gas sensor device in response to the control voltage applied to the control electrode of the gas sensor device during a first clean air phase, a gas insertion phase, a natural recovery phase, and a second clean air phase, wherein the gas insertion phase and the natural recovery phase comprise non-overlapping time intervals;
determining a first gas sensor behavior model based on the measurement values wherein the first gas sensor behavior model comprises a first fitting function comprising a first partial fitting function corresponding only to the gas insertion phase and a second fitting function comprising a second partial fitting function corresponding only to the natural recovery phase;
provide calibration data for the gas sensor device, wherein the calibration data for the gas sensor device is derived from control voltage dependent resistance data over a control voltage range of the gas sensor device;
determining a second gas sensor behavior model based on the calibration wherein the second gas sensor behavior model comprises a second fitting function comprising a first partial fitting function corresponding only to the gas insertion phase and a second fitting function comprising a second partial fitting function corresponding only to the natural recovery phase;
compare the measurement values of the resistance of the gas sensor device with associated calibration data;
adapt, using the first and second gas sensor behavior models, an output signal of the gas sensor device based on a measured difference between the measurement values of the resistance of the gas sensor device and the associated calibration data; and
conduct an automatic baseline calibration of the gas sensor device based on the calibration data stored in a memory device accessible to the processing device, the processing device further configured to:
determine a control voltage dependent measurement value of the resistance of the gas sensitive material having a complete insensitivity to the target gas concentration for different temperatures of at least one of the environmental target gas or the gas sensitive material; and
store the determined control voltage dependent measurement value as a baseline calibration value in the memory device accessible to the processing device if a currently determined baseline calibration value differs from the baseline calibration value stored in the memory device, wherein the baseline calibration value is also independent of the temperature of at least one of the environmental target gas or the gas sensitive material exposed to the target gas.

* * * * *